Figure 1:
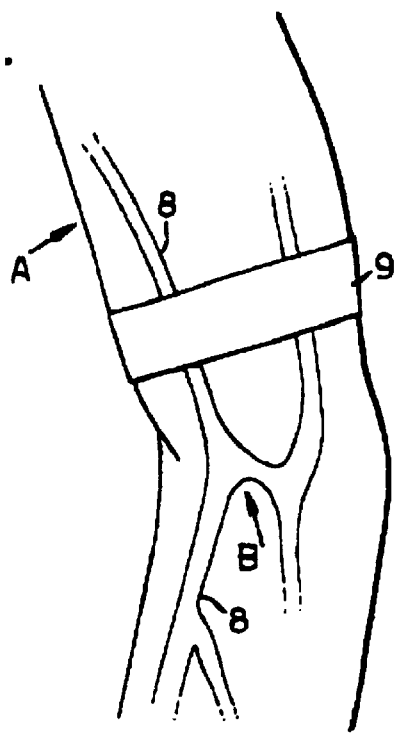

United States Patent
Olaussen

[11] Patent Number: 6,113,568
[45] Date of Patent: Sep. 5, 2000

[54] VEIN CATHETER FOR COAXIAL BLOOD STREAM AND USE OF A SPLIT NEEDLE FOR ITS INTRODUCTION IN A VEIN

[75] Inventor: Richard W. Olaussen, Nesoddtangen, Norway

[73] Assignee: Medinnova SF, Oslo, Norway

[21] Appl. No.: 09/230,696

[22] PCT Filed: Jul. 25, 1997

[86] PCT No.: PCT/NO97/00192

§ 371 Date: Mar. 5, 1999

§ 102(e) Date: Mar. 5, 1999

[87] PCT Pub. No.: WO98/04313

PCT Pub. Date: Feb. 5, 1998

[30] Foreign Application Priority Data

Jul. 31, 1996 [NO] Norway ................................. 963206

[51] Int. Cl.⁷ ...................................... A61M 1/00
[52] U.S. Cl. ........................... 604/27; 264/272; 264/500; 264/523
[58] Field of Search ................................ 604/27, 28, 264, 604/272, 500, 523, 532, 533

[56] References Cited

U.S. PATENT DOCUMENTS 4,096,860  6/1978  McLaughlin .
4,666,426  5/1987  Aigner .
5,480,380  1/1996  Martin .

FOREIGN PATENT DOCUMENTS 0 370 158 A1  5/1990  European Pat. Off. .
502 394  10/1995  Sweden .

OTHER PUBLICATIONS

Deborah J. Brouwer; Cannulation Camp: Basic Needle Cannulation Training for Dialysis Staff; Dialysis & Transplantation; vol. 24, No. 11, Nov. 1995; pp. 606–612.

*Primary Examiner*—John D. Yasko
*Attorney, Agent, or Firm*—Merchant & Gould P.C.

[57] ABSTRACT

An intravenous catheter comprising an inner return tube (1) having return mouth or tip (2) and attached to the return tube (1) an outer access or draw-off tube (3) having draw-off openings (4), where tube (3) and openings (4) are arranged around and coaxial with the inner tube (1), at least along that part which in use is to be inside the vein (8), whereby the distal end of the return tube (1) extends beyond the distal end of the access tube (3), the distance between the return mouth (2) and this distal end preferably being at least twice the width of an approved stasis band.

6 Claims, 8 Drawing Sheets

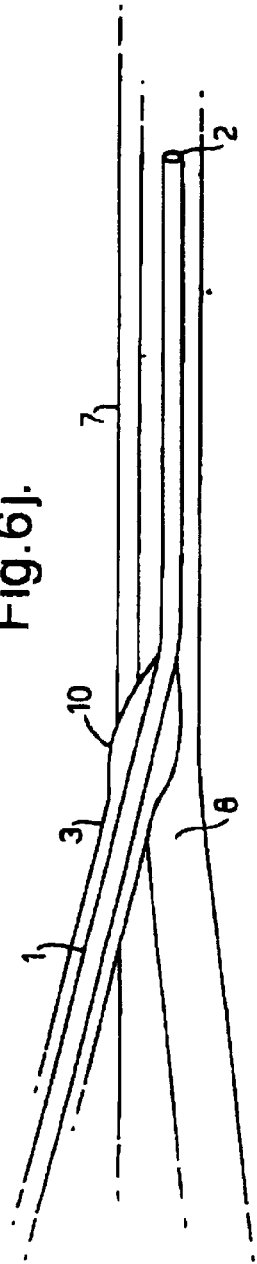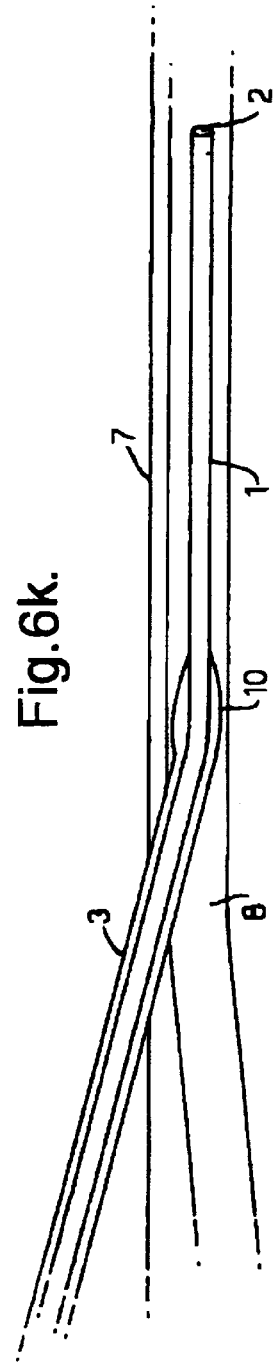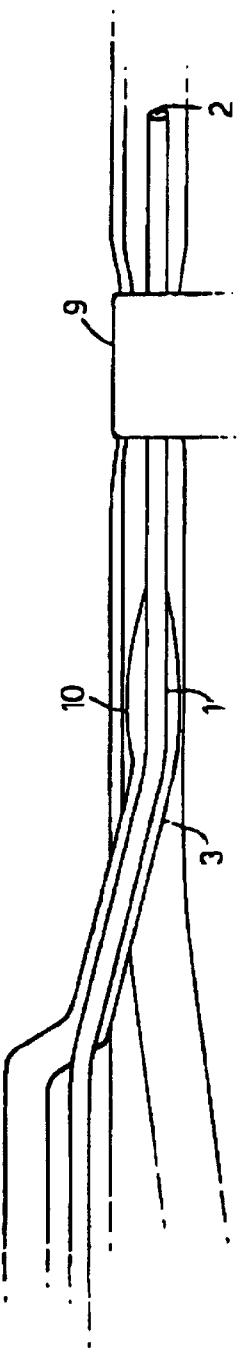

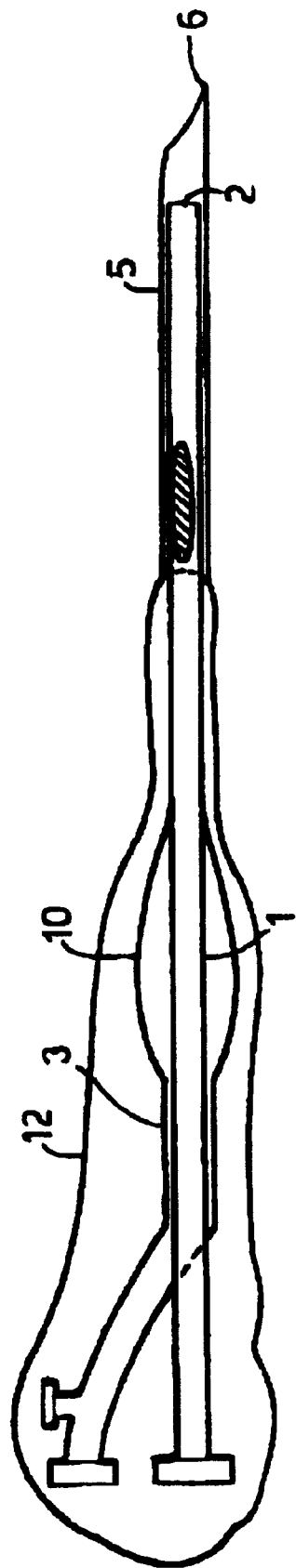

VEIN CATHETER FOR COAXIAL BLOOD STREAM AND USE OF A SPLIT NEEDLE FOR ITS INTRODUCTION IN A VEIN

The present application relates to a intravenous catheter for coaxial bloodflow, especially for use in stem cell aferesis from peripheral blood. The catheter according to the present invention is particularly suitable for aferesis with a view to extracting white blood cells and will be described below with reference to this technology, but the catheter may also be used in the continuous withdrawal from and return to the body of blood which is treated with a view to isolating, for example, blood platelets or various types of white blood cells.

The invention also relates to the use of a split needle for the insertion of this intravenous catheter into a vein.

Stem cells are immature cells which under given circumstances can be stimulated to divide and differentiate to a plurality of more mature cells with very different functions.

Within the context of the invention the term "stem cells" is used to denote cells which are the basis of the cellular elements of blood. These stem cells give rise to red blood cells, white blood cells and platelets and are crucial to the continued and continuous production thereof.

Without stem cells, the levels of white blood cells would drop continuously and unhindered to a dangerously low level, thereby exposing the individual to life-threatening infections that would eventually result in death.

In the same way red cells would gradually die, resulting in death due to lack of oxygen in the tissues.

The level of platelets would also fall and potentially fatal bleeding would ensue.

Cancer can affect cells in the blood, both the stem cells and the later developed, more mature cells. By killing off the blood forming cells with either cytostatics or radiation, and subsequently introducing new stem cells, the patient may be completely cured and health restored to normal. These new stem cells may be taken from another human being (allogenous transplantation) or extracted from the patient (and purified of cancerous cells) prior to the cell destruction procedure. After this procedure the cells are reintroduced (autologous transplantation).

Today there is an increasing demand for stem cells as the above-mentioned stem cell based modes of therapy are developed. Stem cells can be taken from a donor or a patient in two ways.

The first method is based on the stem cells being taken from the bone marrow. Bone marrow harvesting requires general anaesthesia and often produces nausea and local pain in the area of incision through the bone after the procedure. This method also calls for more personnel and material resources. The stem cells harvested will also take longer to establish a thriving, functional bone marrow than stem cells collected from peripheral blood. Risks of infections and other complications are ever-present.

All these drawbacks have resulted in an extensive use of a second method, namely harvesting stem cells from peripheral blood, and on the basis thereof stem cell aferesis has been developed.

Some of the stem cells in the bone marrow percolate into the bloodstream, and normally only a tiny fraction of the white blood cells in the circulating blood are stem cells. In the bone marrow 0.01 to 0.05% of the cells are stem cells and this percentage is even smaller in the peripheral blood.

However, this amount can be increased considerably if the stem cells are mobilised into the bloodstream with different kinds of drugs or factors. This forms the basis for harvesting stem cells from peripheral blood by processing blood taken from a superficial vein immediately below the skin (as opposed to a "central" large vessel deep inside the body and/or close to the heart).

This technology is called Peripheral Blood Stem Cell Aferesis", PBSC aferesis.

In principle, there are two techniques in current use:

1. A suitable amount of blood, normally 400 to 500 ml, is drawn into a machine in a sterile system and processed, a comparatively small amount containing stem cells being held back before the main bulk of the blood is returned to the donor or patient through the same needle. The same procedure is then repeated until a sufficient number of stem cells has been harvested. This technology is called Intermittent Flow Cytaferesis, ICF.

2. The second method is based on blood being drawn from one vein and returned to another vein continuously, normally using a vein in both arms, whilst the blood is processed with a view to stem cell extraction, in the machine. This technology is called Continuous Flow Cytaferesis, CFC.

The blood drawn from the body is processed by spinning in a suitable apparatus, normally either a centrifugal bowl or a ring-formed channel.

Owing to the different specific gravity of the various components of the blood, on centrifugal separation the red cells will be located furthest from the centre. Closer to the centre are the white blood cells, the platelets and the plasma in that order.

The stem cells are in the white blood cell layer and can be collected in different ways after centrifugal separation.

In some IFC machines the separated elements are run through some plastic tubes starting centrally from the top of the centrifugal bowl. Plasma is then sent through the tubes first, and the other elements follow in the reverse order to that mentioned above. Optical density sensors can then detect the different components, and by using different values the desired components can then be channelled into separate collection bags, whilst the rest is returned to the patient or donor.

The CFC machine has a spinning channel and after the separation of the components has been established, the collection begins.

The narrow line between the red blood cells and plasma represents the white blood cells, and this area is called the interface.

It is very important that this interface is stable before collection begins. Any irregularity or abrupt change in the flow parameters (different pumps and valves, changes in the access or return flow from the donor or patient) will cause undulation of this interface, thereby lowering considerably the number of stem cells collected.

This is due to the way in which the stem cells today are collected in this system. Here, a straw-like tube is positioned exactly in this interface, and is used to "suck out" at a very low flow-rate white blood cells containing stem cells.

Today's "single needle" system, as will be described in more detail below, causes major disturbances of this interface and is therefore not recommended.

However, a system where only one needle is used is highly recommendable because of the vastly increased patient or donor comfort associated with such a system.

As such aferesis, i.e., the collection of cells, takes 4 to 5 hours, and sometimes needs to be carried out over two days to obtain enough stem cells, having to keep the elbow stretched and immobilised for so long can be quite uncomfortable and sometimes even painful for the patient or donor.

As far as is known there is today no system or needle which is adapted especially for the purpose of stem cell CFC. The system available, marketed by Gambro, comprises a Y-shaped needle, which as far as is known is the only needle made for single venous access in a peripheral vein, but this needle is made for aferesis of blood platelets. Blood is drawn from the vein through the needle and is processed in the machine before being pumped to a collection chamber with a pressure sensor. When a threshold pressure is reached the access pump stops and the return pump starts up. The blood is then returned to the patient or donor. The volume in the collection chamber is very small, so there is a frequent change in the direction of flow, access I return. Furthermore, the same lumen (i.e., needle) is used for access and return blood, i.e., for unprocessed and processed blood. In principle this is a form of intermittent flow cytaferesis, but the large fluctuations in volume from the donor is avoided. The very large fluctuations in the flow of return and access blood, as mentioned above, causes unmanageable undulations in the interface. This needle is therefore useless for stem cell CFC, and even for platelet aferesis such needles are often not used because they tend to lower the yield of the platelets.

So-called venflons can also be used, although they are not designed for this purpose. In any one case a venflon must be inserted into each arm, one for access blood and one for return blood. Naturally, this limits considerably patient or donor comfort and the danger of spilling blood is present when the tubes are connected to the needle. Sterile conditions are therefore difficult to maintain.

As indicated, the traditional system is a metal needle or cannula in each elbow vein. This is a simple, easy method based on the needles used in ordinary bleeding of donors. However, if this system is used the donor must keep his arms stretched and immobilised for the duration of the aferesis, and this can be extremely unpleasant if the aferesis lasts for several hours. If the arm is moved, the needle may easily fall out of the vein, or even penetrate the other vein wall, causing bleeding in the surrounding tissue. Naturally, the aferesis must then be halted immediately.

The other system that has been used is based on catheters inserted into a central vein, that is a large vein, close to the heart. This approach calls for skilled doctors, anaesthetists or surgeons, an operating theatre and an intensive care ward nearby, and in addition considerably more sterile equipment than required when withdrawing blood from peripheral blood vessels.

The method is time-consuming, requires local anaesthesia and is much more expensive, In addition, the procedure for inserting the central catheter carries a risk of more serious complications. For instance, other vital structures may be perforated, e.g., the lungs, major arteries, nerves etc. Of course, the more skilled the personnel are, the lower the risk. However, because of the prevailing problems, this procedure is only used on patients who are donating stem cells to themselves.

There is therefore a great need for a safe, efficient and sterile system which is easy to use and where the patient or donor preferably may move or flex the arm in use.

Accordingly, the present invention relates to a intravenous catheter for coaxial bloodflow, of the type mentioned above, and this catheter is characterised in that it comprises an inner return tube having a return mouth and an outer access or draw-off tube with draw-off openings, where draw-off tubes and openings are arranged around and substantially coaxial with the inner tube, at least along the part which in use will be inside the vein, whereby the distal end of the return tube extends beyond the distal end of the access tube, the distance between the return mouth or tip and this distal end being preferably at least twice the width of an approved stasis band.

The distance between return tip and draw-off opening is preferably 6 and most preferably about 8 cm.

As mentioned the invention relates to the use of a split needle for insertion of the intravenous catheter described above in to a vein, preferably in the elbow.

From the prior art in this field reference will made to:

1. U.S. Pat. No. 4,096,860, which describes an encatheter for biaxial flow, primarily intended for a haemodialysis process. The patent describes a form of hub having an end piece positioned inside the blood vessel. The hub is inserted with the aid of a hypodermic needle through the centre of the hub and attached thereto by means of a threaded connection. After insertion, the hypodermic needle and associated syringe may be drawn out in such a way that the end piece of the hub remains inside the blood vessel.

Backflow is prevented by a centrally positioned elastic flap or valve, secured by means of an expansion ring. When the syringe has been drawn out, the central tube for backflow of processed blood is inserted. This will go somewhat further in than the hub end piece.

The device is relatively complicated and does not seem to allow continuous withdrawal of unprocessed blood and return of processed blood.

The patent describes a device consisting of very many individual parts, which in addition are in movable relation with one another, i.e., a relatively complex and thus costly apparatus, and furthermore, the system is one which must be characterised as open.

In contrast to this, according to the invention there is provided a catheter which can be made as one unit without movable parts, flaps, special screw or attachment means.

The insertion does not take place with the aid of a conventional syringe or hypodermic needle, and furthermore conventional clips on the tubes, both the return and access tubes will suffice to prevent backflow. The catheter is suitable preferably for being integrated in an aferesis set and it is thus possible to provide a fully closed system, which distinguishes the subject of the invention from the prior art described above and all other prior art.

2. U.S. Pat. No. 4,666,426, which describes a catheter for coaxial flow and having a capacity of as much as 600 ml per minute, designed to be placed in the vena cava very close to the heart, i.e., a central venous access.

The catheter may be as much as 65 to 70 cm in length. Furthermore, there is a description of a two-way connecting member in the rear part of the catheter, and in addition a separate mechanism for stopping the bloodflow as required. This mechanism is shown in the form of a V-flap device. The catheter consists of a plurality of parts and suffers therefore from the same defects as the US patent discussed above, and nor can the patent now under discussion be deemed to be a closed system since there are several possibilities of connection.

The inventive subject described in '426 is intended for central venous access in large and central veins such as the vena femoralis or femoral vein. All dimensions and descriptions are adapted to this purpose and the device is definitely not suitable for the area in which it is the objective of the present invention to work, viz., continuous withdrawal from and return to peripheral veins, preferably elbow veins, with the possibility of applying a stasis. Nor does the patent describe any possibility for closed systems and or for any simple and safe insertion method which makes possible-routine use of blood bank personnel.

Figure 2A:
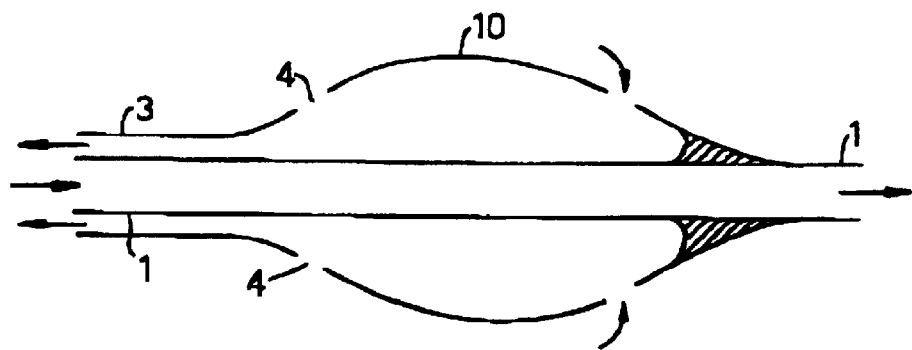
Figure 3:
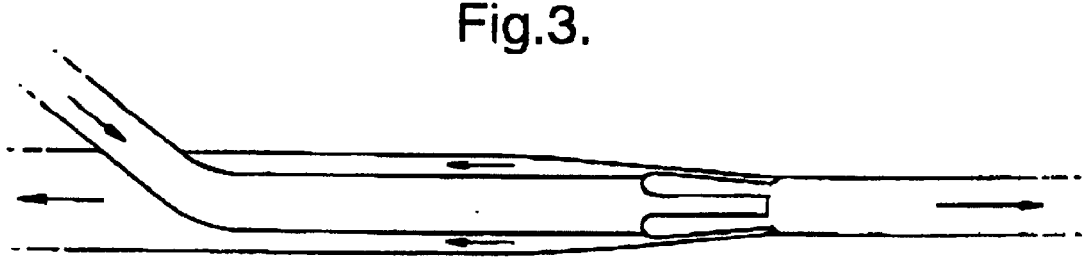
Figure 4:
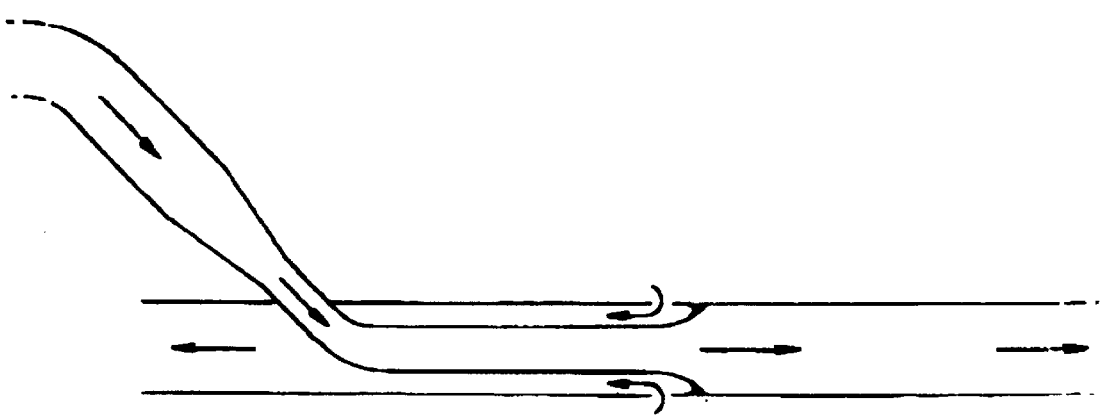
Figure 5:
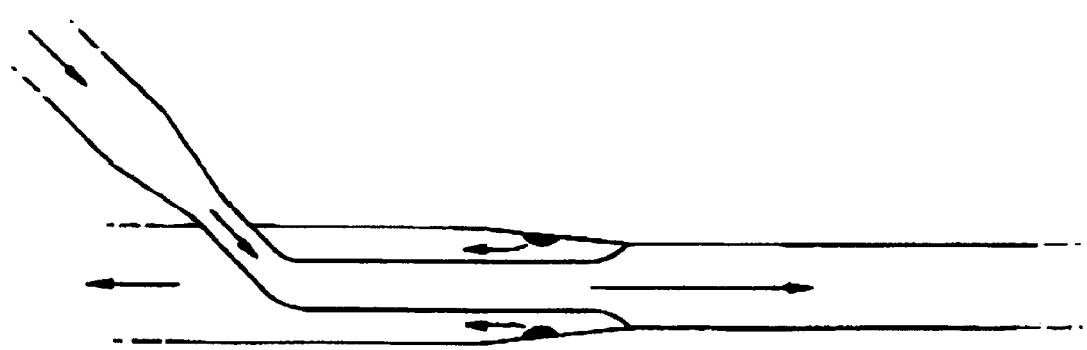
Figure 6A:
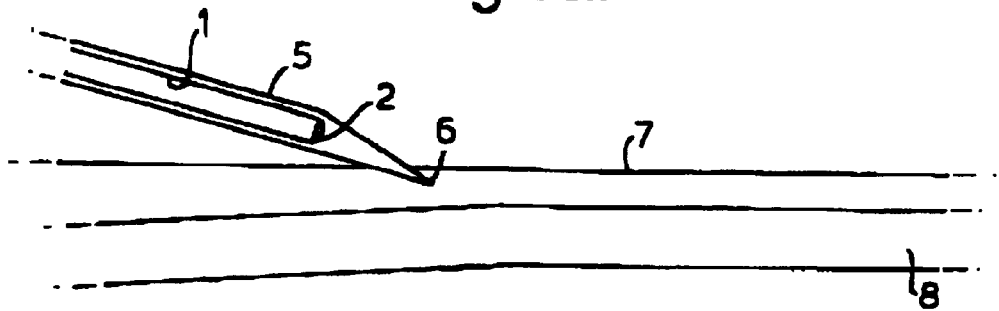
Figure 7A:
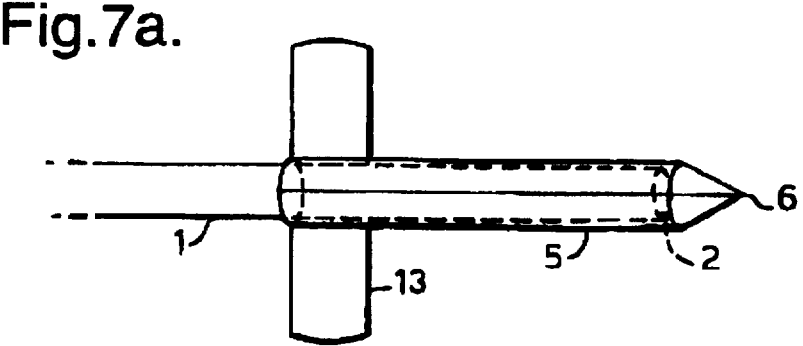

The present invention will be described in more detail with reference to the accompanying drawings, wherein:

FIG. 1 in outline form shows a possible venous course in the area around a human elbow with an applied stasis indicated;

FIGS. 2a) and b) show two alternative embodiments of the area of the intravenous catheter according to the invention where the outer access tube is concentrically attached to and encircles the return tube;

FIGS. 3, 4 and 5 show further embodiments of the intravenous catheter according to the invention;

FIGS. 6a) to l) shows the various steps in the insertion of the catheter;

FIGS. 7a) to d) show the structure and use of an insertion needle in the form of a split needle; and FIG. 8 is a schematic illustration of a possible, sterile way of packaging.

FIG. 1 shows an area around the elbow where superficial veins are indicated. The band 8 represents an elastic stasis. The skin is penetrated at arrow B and, when the catheter of the invention is in place, the tip of the return tube will be approximately at the point indicated by arrow A. The vein is deliberately drawn straight as in nature it often bends in various directions and may also be branched. The mouth of the return tube preferably has slightly rounded edges, and it might also be an advantage if a form of coil is incorporated in the return tube wall, as this can ease the insertion of the catheter. The elasticity makes it possible for the patient or donor to bend his elbow somewhat once the catheter is in place, which of course makes the aferesis more comfortable.

The two alternatives in FIG. 2 show the principle of two possible configurations of the area where the outer access or draw-off tube 3 is concentrically secured to the return tube 1 which lies within and runs the length thereof.

The access tube 3 has in its distal end close to the area of attachment to the return tube 1 a form of a peripheral bulb 10 or bead equipped with access or draw-off openings 4. The shape and structure of the bulb are essential to its function. Specifically, the transition areas between the bulb 10 and the return tube 1, in both the upstream and downstream direction are markedly oblique, in order to facilitate insertion into a vein 8 and also withdrawal therefrom.

The maximum radius of the bulb 10 here is so large that at the point of maximum radius it will abut or lie close to the internal wall of the vein 8. Normally, this will be sufficient to cause the bulk of the blood flow to leave the vein 8 and enter the access tube 3 through the opening 4 for conveying to a non-illustrated processing apparatus with subsequent return through the return tube 1.

The cavity of the bulb 10 may act as a temporary reservoir for the blood, so that fluctuations in the intravenous blood flow are levelled out, although this function may not be very important. FIG. 2a) shows an embodiment where essentially the entire cavity of the bulb 10 is used for the collection of blood and where upstream or downstream of the point of maximum radius there are provided access openings 4 to the access tube 3. Holes downstream may necessitate use of a stasis if the access tube and bulb internally abut the vein wall.

Figure 2B:
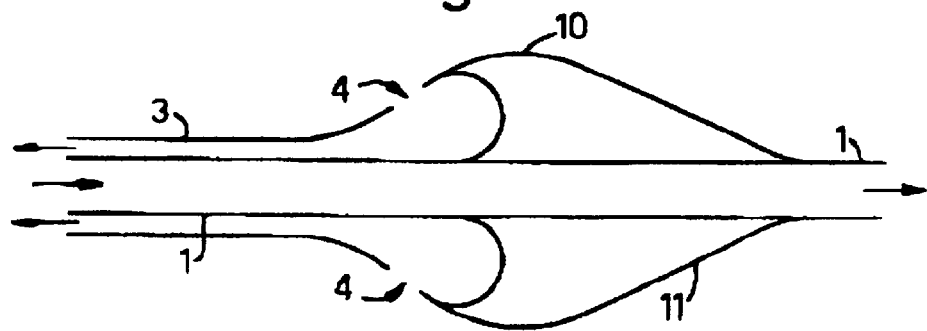

FIG. 2b) shows an alternative embodiment, where the area of transition from the essentially circular-cylindrical upstream part of the unit is slightly sharper, and where the inner lower part of the bulb 10 is filled with a plastic material, and where the downstream "bottom" of the access tube 3 is rounded to aid smooth bloodflow.

Any combinations or variations of the embodiments shown in FIGS. 2a) and b) are conceivable, bearing in mind of course the desired objectives, namely to be able to withdraw blood from the vein 8 smoothly and continuously, without interruptions and also without the bulb 10 collapsing because of negative pressure which is created from the processing apparatus situated downstream.

A collapse of this kind can be counteracted by the embodiment shown in FIG. 2b), where the cavity in the distal end of the bulb 10 on the access tube 3 in the area of attachment to the return tube is filled with a plastic material.

FIGS. 3, 4 and 5 show embodiments of the inventive intravenous catheter where an attempt has been made to give the catheter a slimmer form in order to facilitate the penetration of the access tube through the skin and into the vein.

FIG. 3 shows an embodiment where the access tube 3 has been placed on the outside of the return tube 1 and where the access openings are in the form of slits 4.

These slits must not be too long as blood may be spilled if insertion into the vein is too slow.

FIG. 4 shows an embodiment where a tube downstream is used as return tube 1, whilst upstream of the access openings 4 it serves as access tube 3.

The upstream part of the return tube 1 is passed as a separate tube through the wall in the part serving as access tube and exactly downstream of the access opening 4 is attached internally to the tube which now constitutes the return tube 1.

FIG. 5 shows a combination of the embodiments in FIGS. 3 and 4, inasmuch as the radius of the access tube downstream of the access openings has been made slightly larger, thereby producing a slightly increased volume of blood.

The insertion procedure for the inventive catheter will be described in greater detail in FIGS. 6a) to 6l).

FIG. 6a) shows an insertion needle 5 in the form of a split needle, which in a starting position encircles the return tube I and the return mouth 2.

The tip 6 of the needle 5 has penetrated the skin 7.

Figure 6B:
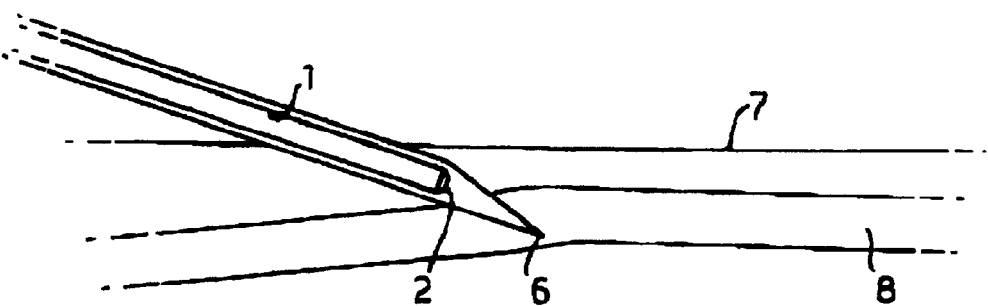

FIG. 6b) shows the situation once the needle 5 has been inserted further and has penetrated into the vein 8. Venous blood will now flow into the return mouth 2 and flow in the direction of the processing machine. How far back the blood is allowed to flow can be controlled by conventional, non-illustrated clips, which can be manipulated in a simple manner to be opened and closed as desired.

Figure 6C:
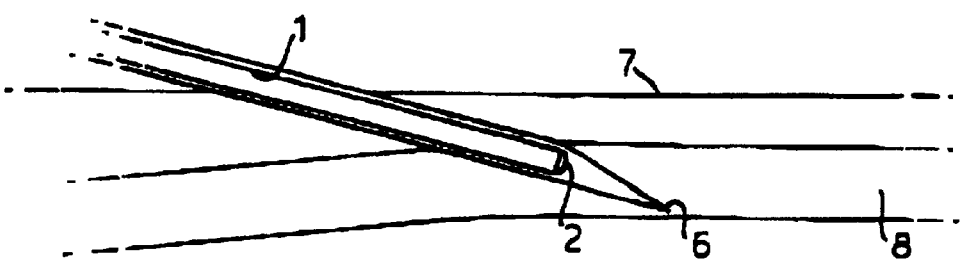

FIG. 6c) shows the situation when the needle 5 is fully inserted into the vein 8. It is not until this point that the return tube 1 should be pushed into the split needle 5.

Figure 6D:
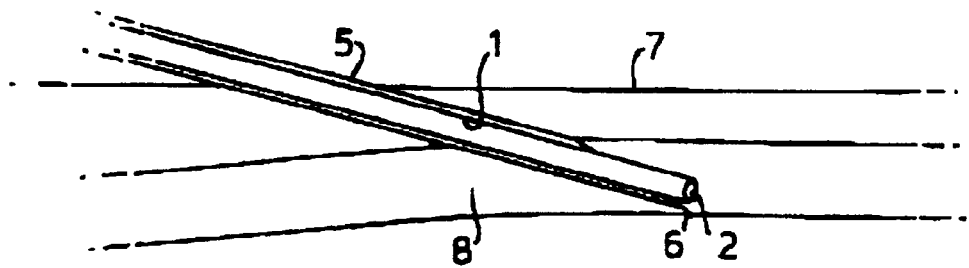

In FIG. 6d) the return tube 1 begins to penetrate into the vein.

In order to ensure a smooth and problem-free insertion into the vein 8, it is an advantage if the mouth 2 of the return tube 1 has slightly rounded edges, and it might also be an advantage if the walls of the return tube are slightly stiffened, for example, by means of a suitable coil.

Figure 6E:
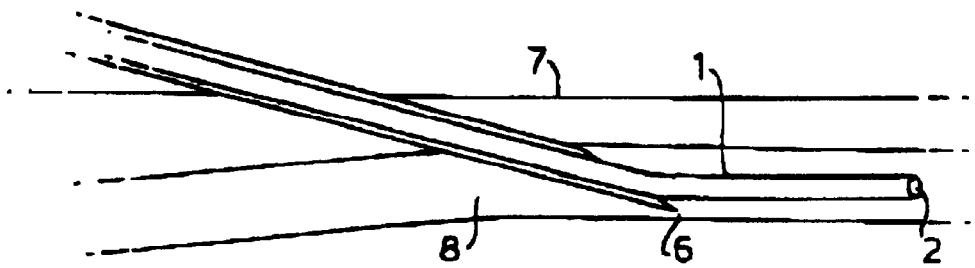
Figure 6F:
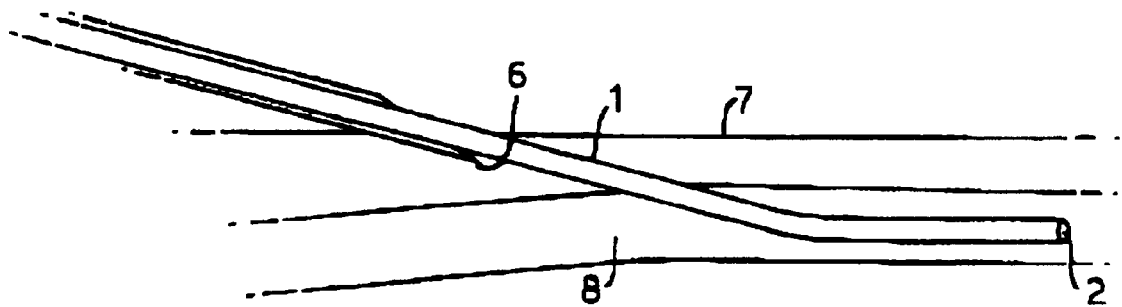
Figure 6G:
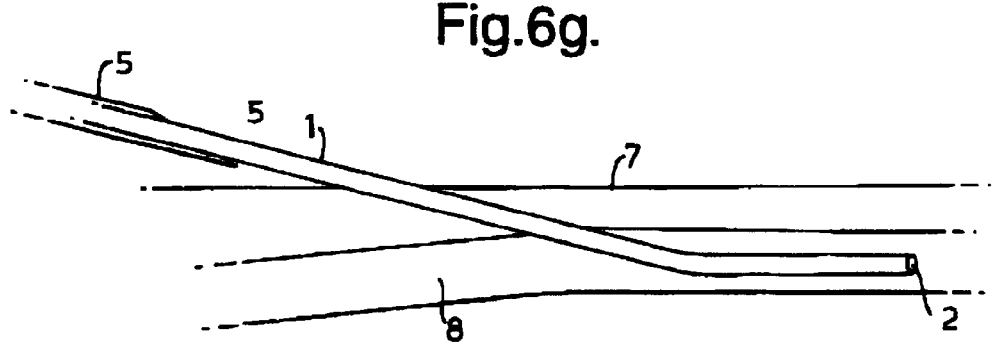

At this point it is of crucial importance that the insertion needle 5 is held still and in position so that it does not slip out of the vein 8 or perforate the vein wall. FIG. 6e) shows a situation where the return tube 1 has been passed so far into the vein 8 that the withdrawal of the needle 5 may begin and the needle is gradually pulled all the way out, as shown in FIGS. 6f) and g).

Figure 6H:
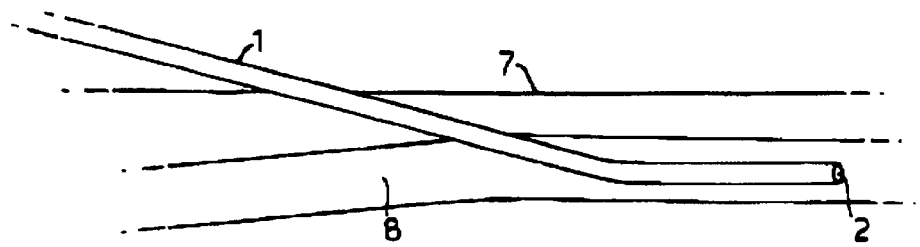
Figure 6I:
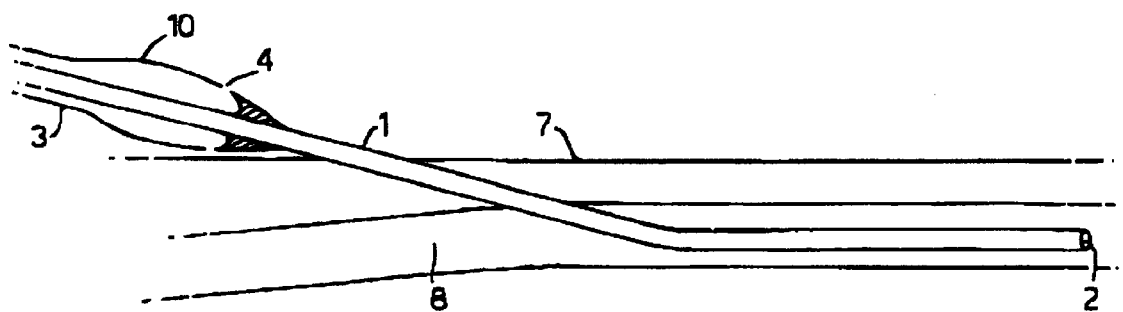

In FIG. 6h) the insertion needle 5 has split fully into two parts and has been disposed of, and the insertion of the return tube 1 continues as indicated in FIG. 3i), which shows the situation immediately prior to the access tube 3 with its oblique shape being ready for insertion through the skin 7 and into the vein 8.

A situation of this kind is shown in FIG. 6l). The bulb 10 of the access tube 3 in the distal end pierces through the skin 7 because of its oblique shape and the skin seals the widened hole after the passage of the bulb because of its inherent elasticity. Once the bulb 10 of the access tube 3 and associated openings 4 are inside the vein 8, blood will begin to flow into the access tube 3 in the direction of the processing machine. Again, conventional, non-illustrated clips may be used to regulate the backflow as desired.

FIG. 6k) shows the situation when both the return tube 1 and the access tube 3 have been put in place inside the vein 8. A possible sterile bag 12 (see below, FIG. 5) may now be removed and the parts of the apparatus that are outside the body are connected to tubings which run to and from the processing apparatus. For this purpose, the return tube 1 is now passed out of the access tube 3, as indicated to the left in FIG. 6l).

To build up pressure in the vein 8 and to prevent an excess of blood from flowing past the openings 4 of the access tube 3, a stasis 9 is applied approximately half way between the distal bulb 10 of the access tube 3 and the distal mouth or tip of the return tube 1. The free end of the return tube 1 is preferably at least twice the width of an approved stasis band 9, and most preferably the return tube 1 has a free part in the vein which is about three times the width of an approved stasis band 9.

In this position the blood 8 flows from the machine through the access tube 3. The arterial pressure, that is the pumping effect of the dynamic muscle contractions in conjunction with the unidirectional valves in the vein, guarantees a slight positive pressure of about 20 mm Hg in the vein. The blood flows "slowly" back towards the heart. It is this bloodflow that must be interrupted so that the blood enters the access openings 4, whence the blood is drawn to the processing machine. The venous bloodflow is reestablished on the other side of the catheter of the invention. To increase intravenous pressure around the opening 4 of the access tube 3 a stasis is applied. With the aid thereof it is ensured that in addition to increased pressure non-processed and processed blood are not mixed. The vessel walls cling to the return tube 1 at the stasis site. Pressure is applied both to the subcutaneous tissue area and to the deep tissue area, however the vein 8 suffers no damage because the aferesis using this method requires a relatively short time.

It should be unnecessary to mention that the catheter of the invention is made of a medically speaking compatible material.

The internal diameter of the return tube 1 should be about 1.2 to 1.4 mm. The flow resistance must be adapted to the pumping effect of the machine, and since resistance is inversely proportional to the square of the radius, this is a critical point as the diameter is of course also limited by normal vein sizes. The resistance is also proportional to the length of the tube, but a free length of the return tube 1 in the vein 8 downstream of the distal end of the access tube 3 of about 6 to 10 cm, preferably 8 cm, has proved to be favourable according to the invention. A further limitation on the external diameter of the return tube 1 is of course the vein size, seen in connection with the distal end and bulb 10 of the access tube 3.

The return tube 1 must be made of a material that has sufficient mechanical strength to resist the pressure that is applied when a stasis is applied and, as mentioned above, this can be achieved by, for example, embedding a coil of a suitable material in the return tube 1.

The insertion needle 5 for first inserting the return tube 1 and then the access tube 3 in a vein 8 is illustrated in FIGS. 7a) to d).

FIG. 7a) shows a split needle 5 in the form of a pointed sleeve encircling the distal end of the return tube 1. At the rear edge the needle is equipped with two wings 13 of a conventional type to facilitate the grip around and insertion of the needle 5 into a vein 8.

Figure 7B:
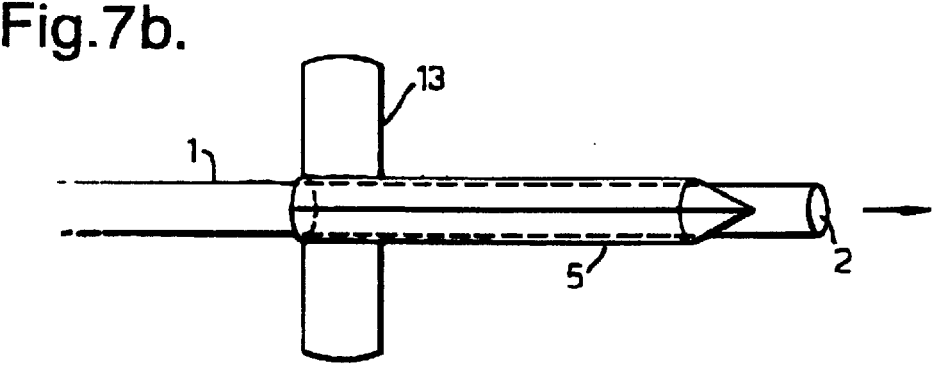
Figure 7C:
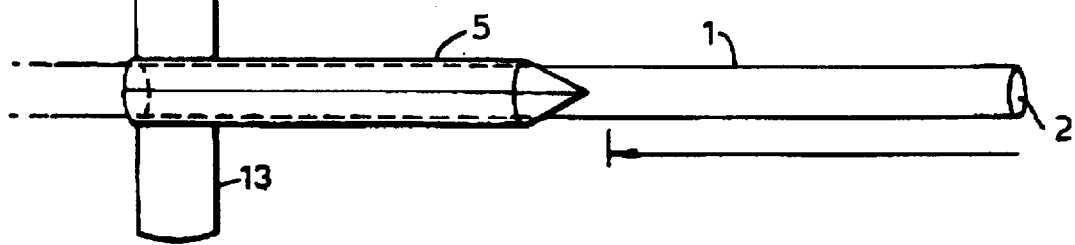

When the needle, as shown in FIG. 3 c) is fully inserted into the vein 8, the return tube 1 is pushed forward, as shown in FIGS. 6d) and 7b). The distal end of the insertion needle permits free passage of the return tube 1, as indicated by an arrow in FIG. 7b).

Figure 7D:
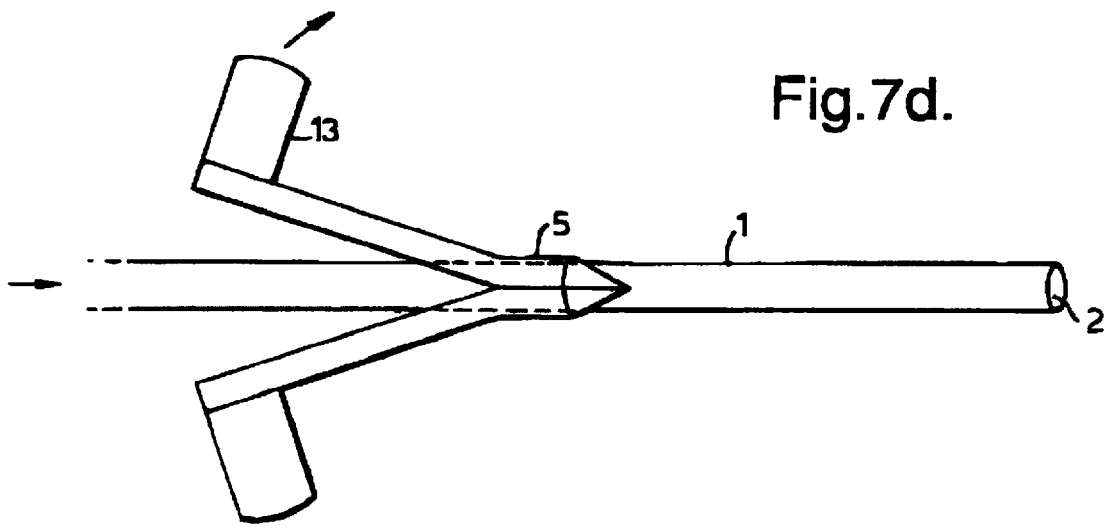

After sufficient insertion of the return tube 1 into the vein 8, the split needle 5 is drawn back, as indicated in FIGS. 6f), 6g) and 7c), and finally the split needle 5 is split completely as indicated in FIG. 7d), whereupon the two parts are disposed of.

The split needle 5 is of a conventional type per se where the two halves are secured to one another in a suitable manner along the diametrically disposed, longitudinal seams.

Well-trained health personnel have no difficulties in manipulating this type of needle.

Finally, FIG. 8 shows a possible packaging unit where everything which is upstream of the insertion needle 5 is enveloped by a stocking or bag 12.

The catheter of the invention and also the bag 12 are of a material which permits sterilisation, and when in addition the insertion needle 5 is enveloped by a nonillustrated protective sleeve, which allows sterilisation of the catheter and needle, this means that the unit of the invention and associated equipment can be delivered in a sterile condition for rapid, speedy connection to machines. Since the device in addition is so simple that it can be used by reasonably well-trained health personnel, this means that this mode of treatment can be moved from hospitals and out among the general public, i.e., to, for example, local health centres, which in turn will mean a considerable improvement of efficiency with a view to being able to use to a maximum the resources which are represented by voluntary blood donors.

What is claimed is:

1. A catheter device, comprising a return tube and an access tube having a distal end and draw-off openings, wherein said access tube is substantially co-axial to said return tube at least along that part which is to be inside a vein and wherein the distal end of the return tube extends beyond the distal end of the access tube by a length of at least 4.5 cm whereby mixing of access and return blood is prevented.

2. A catheter according to claim 1, wherein the distal end of the return tube extends beyond the distal end of the access tube by a length of at least about 6 cm.

3. The use of a split needle for insertion of a intravenous catheter according to claim 1.

4. A catheter according to claim 2, wherein the distal end of the return tube extends beyond the distal end of the access tube by a length of about 8 cm.

5. A catheter device, comprising a return tube having at least one outlet opening for return blood, and an access tube having a distal end and draw-off openings, wherein said access tube is substantially co-axial to said return tube at least along that part which is to be inside a vein, and wherein no outlet opening in the return tube is closer than 4.5 cm to the distal end of the access tube.

6. A catheter device according to claim 5, wherein said return tube includes a single said outlet opening, and said single outlet opening is disposed at said distal end of said return tube.

* * * * *